US005686278A

United States Patent [19]
Williams et al.

[11] Patent Number: 5,686,278
[45] Date of Patent: Nov. 11, 1997

[54] METHODS FOR ENHANCED RETROVIRUS-MEDIATED GENE TRANSFER

[75] Inventors: David A. Williams, Indianapolis, Ind.; Vikram P. Patel, Olney, Md.

[73] Assignee: Indiana University Foundation, Bloomington, Ind.

[21] Appl. No.: 218,355

[22] Filed: Mar. 25, 1994

[51] Int. Cl.⁶ ............................ C12N 15/09; C12N 5/10
[52] U.S. Cl. .................................. 435/172.3; 435/372
[58] Field of Search ............................ 435/69.1, 240.2, 435/172.1, 172.3, 320.1, 325, 366, 372, 372.1, 372.2, 372.3

[56] References Cited

PUBLICATIONS

Patel, V.P. and Lodish, H.F., "The Fibronectin Receptor On Mammalian Erythroid Precursor Cells: Characterization and Developmental Regulation", *J. Cell. Biol.*, vol. 102, pp. 449–456 (1986).

Ruoslahti, E., Hayman, E.G. and Engvall, E., "Alignment Of Biologically Active Domains In The Fibronectin Molecule", *J. Biol. Chem.*, vol. 256, pp. 7277–7281 (1981).

Moritz, T., Keller, D.C. and Williams, D.A., "Human Cord Blood Cells As Targets For Gene Transfer: Potential Use In Genetic Therapies Of Severe Combined Immunodeficiency Disease", *J. Exp. Med.*, vol. 178, pp. 529–536 (1993).

Lim, B., Apperley, J.F., Orkin, S.H. and Williams, D.A., "Long–Term Expression Of Human Adenosine Deaminase In Mice Transplanted With Retrovirus–Infected Hematopoietic Stem Cells", *Natl. Acad. Sci., U.S.A.*, vol. 86, pp. 8892–8896 (1989).

Markowitz, D., Goff, S. and Bank, A., "Construction And Use Of A Safe And Efficient Amphotropic Packaging Cell Line", *Virology*, vol. 167, pp. 400–406 (1988).

Bernardi et al., "Lymphoid Precursor Cells Adhere to Two Different Sites on Fibronectin", *J. Cell Biol.*, vol. 105, Jul., pp. 489–498 (1987).

Sutherland et al., "Characterization and Partial Purification of Human Marrow Cells Capable of Initiating Long–Term Hematopoiesis In Vitro", *Blood*, vol. 74, No. 5, pp. 1563–1570 (1989).

Toksoz et al., "Support of Human Hematopoiesis in Long-–Term Bone Marrow Cultures by Muring Stromal Cells Selectively Expressing the Membrane–Bound and Secreted Forms of the Human Homolog of the Steel Gene Product, Stem Cell Factor", *Proc. Natl. Sco. USA*, vol. 89, Aug., pp. 7350–7354 (1992).

*Primary Examiner*—David Guzo
*Attorney, Agent, or Firm*—Woodard, Emhardt, Naughton, Moriarty & McNett

[57] ABSTRACT

A method to increase the efficiency of transduction of hematopoietic cells by retroviruses includes infecting the cells in the presence of fibronectin or fibronectin fragments. The fibronectin and fibronectin fragments significantly enhance retroviral-mediated gene transfer into the hematopoietic cells, particularly including committed progenitors and primitive hematopoietic stem cells. The invention also provides improved methods for somatic gene therapy capitalizing on the enhanced gene transfer, and hematopoietic cellular populations.

22 Claims, 3 Drawing Sheets

METHODS FOR ENHANCED RETROVIRUS-MEDIATED GENE TRANSFER

This invention was made with government support under National Institute of Health Grant Nos. RO1 HL-46528 and PO1 HL-45168. The government has certain rights in this invention.

FIELD OF THE INVENTION

The present invention relates generally to methods for increasing the efficiency of transduction of hematopoietic cells by retroviruses, and more particularly to methods for enhancing retroviral-mediated gene transfer into hematopoietic cells utilizing fibronectin and/or fibronectin fragments.

BACKGROUND OF THE INVENTION

Progress in understanding the molecular basis of many human diseases as well as improvement in gene transfer technology has led to recent attempts to develop protocols for somatic gene therapy for severe genetic diseases. Currently, promising disease candidates for human gene therapy include those in which an enzyme or other protein is defective or missing, where the level of enzyme or protein does not need to be exactly regulated, especially those that are constitutively regulated, and those defects which are found in the patient's bone marrow.

For example, one disease candidate for gene therapy is adenosine deaminase (ADA) deficiency which results in severe combined immunodeficiency disease (SCID). ADA deficient patients have little or no detectible enzyme in bone marrow cells. However, ADA deficiency has been cured by matched bone marrow transplantation. ADA normal cells have a selective advantage over ADA deficient cells and will normally repopulate the patient's bone marrow.

Bone marrow cells are a good target for somatic gene therapy because bone marrow tissue is easily manipulated in vitro and contains repopulating cells. Alternatively, human cord blood has previously also been demonstrated to contain a large number of primitive progenitor cells. Successful gene transfer into hematopoietic stem cells, the long term repopulating cells, may lead to lifelong cures for a variety of diseases manifested in the progeny of these cells.

Gene transfer into, and long term gene expression in, repopulating stem cells has been achieved in murine models by a number of investigators. However, in vivo experiments in larger animals, such as dogs and primates, have met with limited success, largely due to the low efficiency of infection of primitive hematopoietic stem cells. The limitations of current gene transfer technology are further complicated when applied to human protocols by several factors, including the low numbers of stem cells present in adult bone marrow (ABM), the lack of suitable methods purify these cells, and the low fraction of such primitive cells in cell cycle.

In both murine and large animal experiments involving bone marrow cells, it has been noted that the most successful protocols utilize cocultivation of target cells with retroviral producer cell lines. Also, most of the FDA-approved gene transfer trials in humans rely on recombinant retroviral vectors for gene transduction. Recombinant retroviral vectors are desireable for gene therapy because they efficiently transfer and precisely and stably integrate exogenous DNA into cellular DNA. These vectors contain exogenous DNA for gene transfer and are further modified to eliminate viral pathogenicity. Because of these modifications, viral production is generally accomplished using retrovirus packaging cells. However, for clinical gene therapy, cell-free transduction is more desirable due to concerns about bio-safety and quality control. Unfortunately, efficient gene transfer into hematopoietic cells such as stem cells has generally not been possible without cocultivation with virus-producing cells.

Recently, it has been shown that gene transfer efficiency can be increased by exposing target cells to stromal cells during infection. Stromal cells are a major component of the hematopoietic microenvironment (HM). The HM consists of an organized network of macrophages, stromal cells, endothelial cells, adipocytes and a complex extracellular matrix made up of a variety of defined adhesion molecules. ECM molecules such as laminin, collagen, thrombospondin, proteoglycans, glycosaminoglycans and fibronectin provide anchorage sites for both hematopoietic cells and growth factors. The mechanism underlying this promoting effect of stroma on retroviral infection is unclear, but it has been known for some time that physiologic regulation of the proliferation and differentiation of hematopoietic cells occurs when these cells are in direct contact with cells of the HM.

Efficient gene transfer into long term repopulating hematopoietic stem cells remains problematic, inhibiting the widespread application of gene transfer protocols for curative therapy of hematopoietic disease at present. A need persists for methods for efficient transfer of genetic material into mammalian cells without the dangers and limitations of past methods. The present invention addresses these needs.

SUMMARY OF THE INVENTION

Briefly, one preferred embodiment of this invention provides a method for increasing the frequency of transduction of hematopoietic cells by a retrovirus vector. The method includes infecting hematopoietic cells with a replication-defective recombinant retrovirus vector in the presence of substantially pure fibronectin and/or fibronectin fragments effective to increase the frequency of cellular transduction by the retrovirus.

Another preferred embodiment of the invention provides a method for producing transduced hematopoietic cells which includes infecting hematopoietic cells with a replication-defective recombinant retrovirus carrying exogenous DNA in the presence of immobilized fibronectin, immobilized fibronectin fragments, or an immobilized mixture thereof effective to increase the frequency of cellular transduction by the retrovirus.

Another preferred embodiment of the invention provides an improved method for cellular grafting. The method includes the steps of obtaining hematopoietic cells from an animal donor; infecting the hematopoietic cells with a recombinant retrovirus vector to produce transduced hematopoietic cells, the infecting being in the presence of fibronectin and/or a fragment thereof in immobilized form and effective to increase the frequency of transduction; and introducing the transduced hematopoietic cells into an animal recipient as a cellular graft. In a preferred mode the infected cells can be introduced into an autologous donor.

Still other preferred embodiments of the invention generally provide hematopoietic cellular cultures containing substantially pure and/or immobilized fibronectin or fragments thereof.

It is an object of this invention to provide a method for efficient retroviral infection of mammalian cells.

It is a further object of this invention to provide a method for gene transfer with retroviral vectors which avoids the need for cocultivation.

It is a further object of the invention to provide improved methods for autologous cellular grafting.

These and other objects, advantages, and features of the invention will be readily apparent from the following description.

DESCRIPTION OF THE PREFERRED EMBODIMENT

Figure 1:
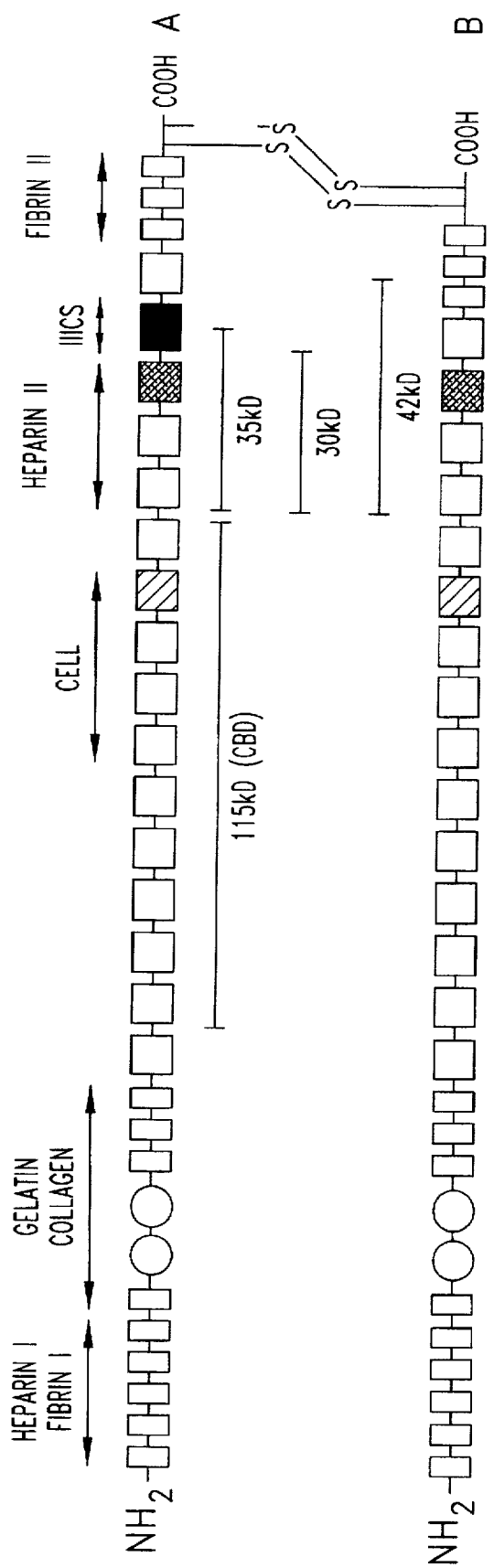
FIG. 1 shows a schematic representation of a fibronectin molecule, including chymotryptic fragments.

For the purpose of promoting an understanding of the principles of the invention, reference will now be made to certain embodiments and specific language will be used to describe the same. It will nevertheless be understood that no limitation of the scope of the invention is thereby intended, such alterations, further modifications and such applications of the principles of the invention as illustrated herein being contemplated as would normally occur to one skilled in the art to which the invention relates.

As indicated above, the present invention provides methods for increasing the frequency of transduction of hematopoietic cells by retroviruses. The invention also provides methods for efficient gene transfer into hematopoietic cells using recombinant retroviral vectors, methods for obtaining transduced cells, and methods for achieving autologous and other cellular grafts.

A feature of the present invention is the discovery that fibronectin (FN), and chymotryptic fragments of fibronectin containing the alternatively spliced CS-1 adhesion domain of FN, significantly enhance retroviral-mediated gene transfer into cells such as hematopoietic cells, e.g. committed progenitors and primitive hematopoietic stem cells or long-term culture-initiating cells (LTC-IC), carrying the fibronectin receptor. Advantageously, this increased efficiency makes cocultivation with virus-producing cells unnecessary.

Recombinant retroviral vectors in accordance with the present invention contain exogenous DNA and are non-pathogenic, i.e. replication-defective. These vectors efficiently transfer and precisely and stably integrate exogenous DNA into cellular DNA of host animal cells. For example, in the present invention a nucleotide sequence including a run of bases from the coding sequence of the gene of interest can be incorporated into a recombinant retroviral vector under the control of a suitable promotor to drive the gene, typically an exogenous promoter. In this regard, the exogenous DNA can contain DNA which has either been naturally or artificially produced, and can be from parts derived from heterologous sources, which parts may be naturally occurring or chemically synthesized molecules, and wherein those parts have been joined by ligation or other means known to the art. As indicated, the introduced nucleotide sequence will be under control of a promoter and thus will be generally downstream from the promoter. Stated alternatively, the promoter sequence will be generally upstream (i.e., at the 5' end) of the coding sequence. In this vein, it is well known that there may or may not be other regulatory elements (e.g., enhancer sequences) which cooperate with the promoter and a transcriptional start codon to achieve transcription of the exogenous coding sequence. The phrase "under control of" contemplates the presence of such other elements as are necessary to achieve transcription of the introduced gene. Also, the recombinant DNA will preferably include a termination sequence downstream from the introduced coding sequence.

Retroviral vectors that include exogenous DNA providing a selectable marker or other selectable advantage are preferred. For example, the vectors can contain one or more exogenous genes that provide resistance to various selection agents including antibiotics such as neomycin. Representative vectors which can be used in the invention include the $N_2$/ZipTKNEO vector (TKNEO) (titer: $1 \times 10^5$ G418$^r$ cfu/ml on NIH 3T3 cells), the ZipPGK-hADA vector, and the ZipPGK-mADA vector all as previously reported by Moritz et al. (1993) *J. Exp. Med.* 178:529. In the TKNEO vector, neo phosphotransferase sequences are expressed in the sense orientation (relative to the 5' long terminal repeat-LTR) via the herpes simplex thymidine kinase promoter. This vector contains a selectable maker gene which provides neomycin resistance to facilitate the identification of transduced cells. In the ZipPGK-hADA vector, the hADA cDNA is expressed in the sense orientation relative to the 5'LTR via the human phosphoglycerate kinase (PGK) promoter. It contains only one expressable genetic sequence and lacks a dominant selectable marker. The ZipPGK-mADA (PGK-mADA) vector is identical to the ZipPGK-hADA vector except the human ADA cDNA has been replaced with murine ADA DNA. These and other retrovirus vectors and techniques for their production are well known and their implementation and use in the present invention will be well within the skills of those practiced in the art given the disclosure herein.

As indicated above, methods of the present invention are advantageously conducted without the need for cocultivation. Thus, in accordance with one aspect of the invention, the retroviral-mediated gene transfer can be carried out in the substantial absence of cells other than the target hematopoietic cells. For example, producer cells containing the retroviral vector plasmid can be cultured and supernatant collected. The retroviral-containing supernatant can then be utilized to infect the hematopoietic cells in the presence of the fibronectin and/or fibronectin fragments, which are preferably in immobilized form, e.g. coated on a substrate upon which the infection is carried out. In this regard, any producer cells which produce high-titer helper-free retroviruses are contemplated as suitable for use in the invention. These include, for example, packaging cells such as Ψ2, PA12, PA317, and GP+envAM12.

Chymotryptic fragments of fibronectin for use in the invention can be of natural or synthetic origin, and can be prepared in substantially purity for example as previously described by Ruoslahti et al. (1981) *J. Biol. Chem.* 256:7277; Patel and Lodish (1986) *J. Cell. Biol.* 102:449; and Bernardi et al. (1987) *J. Cell Biol.* 105:489. In this regard, reference herein to a substantially pure fibronectin or fibronectin fragments is intended to mean that they are essentially free from other proteins with which fibronectin naturally occurs. Fibronectin fragments which contain the alternatively spliced CS-1 cell adhesion domain, e.g. about a 30 or 35 kd fragment (30/35 FN) as reported in the Examples below, have been found to significantly increase gene transfer into hematopoietic cells in work thus far, and are preferred for use in the invention.

One aspect of the invention provides a method of somatic gene therapy which involves in-vitro cellular therapy and transplantation into a host. Hematopoietic cells can be collected from a human or other mammalian or animal source using standard protocols. For example, the hematopoietic cells can be collected from donor bone marrow or peripheral blood or from animal, e.g. human, fetal cord blood. Once collected, the hematopoietic cells can optionally be treated so as to enrich them in stem cells and/or primitive progenitor cells. The hematopoietic cells can then be suitably incubated, for instance on tissue culture plates. Optionally during this period, adherent-negative low density mononuclear cells can be prestimulated prior to retroviral infection. Prestimulation as used herein refers to the process of exposing cells to growth stimulating factors before exposure to retroviruses.

Subsequent to prestimulation, the cells can be harvested and incubated with fibronectin or fragments thereof which enhance the frequency of cellular transduction by retroviruses. Preferably, the cells are incubated with purified and/or immobilized fibronectin or a fibronectin fragment containing the alternatively spliced CS-1 cell adhesion domain of fibronectin. The cells can then be infected with the recombinant retrovirus, the retrovirus for instance containing a gene for correcting an enzyme or other protein deficiency or abnormality in the cells, in the presence of the fibronectin or a fragment thereof. The resulting transduced hematopoietic cells can then be conventionally introduced, e.g. intraveneously, into an animal cellular graft recipient, preferably an autologous donor.

Methods of the invention can be used in gene marking or gene therapy protocols for a variety of bone marrow disorders, including for example cancers, leukemias, disorders involving protein deficiencies or abnormalities, and for modifying hematopoietic cells to improve resistance to other therapeutic protocols such as chemotherapy. Representative disorders with which the invention may be used thus include ADA deficiency, e.g. ADA-deficient SCID, pediatric acute myelogenous leukemia (AML), neuroblastoma, and adult AML and acute lymphocytic leukemia (ALL).

If desired, harvested transduced hematopoietic cells can be tested for transduction efficiency and gene expression. For instance, the significant improvements in retrovirus-mediated gene transfer provided by the invention are demonstrated in the specific Examples below, which describe several tests demonstrating high infection and gene transfer efficiency by retroviruses in the presence of fibronectin or effective fibronectin fragments. In particular, murine hematopoietic cells infected with PGK-hADA retrovirus expressed high levels of the transferred ADA CDNA. Similarly, individual PGK-mADA virus infected progenitor colonies expressed murine ADA levels up to 10-fold higher than the endogenous human ADA protein. Therefore, to stringently analyze transfer efficiency, progenitor colonies were considered transduced only if expression of the transferred mADA was equal to or greater than endogenous human ADA levels. High levels of expression of neo from the TKNEO vector were detected by G418 drug resistance, as an assay for neophosphotransferase (the neo gene product) activity.

In order to promote a further understanding and appreciation of the invention, the following specific Examples are provided. It will be understood that these examples are illustrative and not limiting in nature.

EXAMPLE 1

Gene Transfer into Bone Marrow Cells Using TKNEO
Preparation of Virus-Supernatant GP+EnvAM 12 producer cells (see Markowitz et al. (1988) *Virology* 167:400) containing retroviral plasmid TKNEO vector were cultured in Iscove's Modified Dulbeccos Medium (IMDM, Gibco, Gaithersburg, Md.) containing 10% fetal calf serum (FCS, Hyclone, Logan, Utah) and 100 units/ml penicillin and 100 microgram/ml streptomycin (P/S, both Gibco). Virus containing supernatant was collected by adding 10 ml of IMDM containing 20% FCS to confluent plates overnight. Harvested medium was filtered through 0.45 micron filters (Gelman Sciences, Ann Arbor, Mich.) and stored at −80° C. until used.

Preparation of fibronectin fragments

FN was purified from human plasma (Lifesource, Glenview, Ill.) as previously described in Ruoslahti et al. (1982), except that the gelatin-agarose column was washed with 1 M urea prior to elution of FN with 4 M urea. Purified FN was dialyzed extensively at 4° C. against 10 mM 3-(cyclohexylamino)-1-propane-sulfonic acid (CAPS), 150 mM NaCl, 2 mM $CaCl_2$ pH 11.0 and stored in aliquots at −80° C. The chymotryptic cell binding domain (CBD) and heparin-binding fragments of FN were purified as previously described (Ruoslahti et al. (1982), Patel and Lodish (1986), and Bernardi et al. (1987). Three major heparin-binding fragments (30 kD, 35 kD, and 42 kD) were obtained in the 1 M NaCl eluate from the heparin-agarose column. To further purify these heparin-binding fragments, the 1 M NaCl eluate was dialyzed overnight at 4° C. against 10 mM Tris-HCl, pH 7.0 and passed over an anion exchange column (2 ml DEAE sepharose fast flow (Pharmacia Fine Chemicals, Uppsala, Sweden)/mg of protein) that had been equilibrated with 10 mM Tris-HCl pH 7.0. The 30/35 kD fragments were collected in the unbound fraction while the 42 kD fragment was eluted from the column with 100 mM NaCl. From 500 mg of FN, approximately 26 mg of the 30/35 kD fragments and 4 mg of the 42 kD fragment were obtained. The 42 kD fragments, but not the 30/35 kD fragments, were recognized by an antibody against the fibrin-binding domain, as determined by western blotting technique. Also, the 42 kD fragment binds to a fibrin-sepharose affinity column.

For use in the infection protocol, fibronectin fragments were immobilized on 35 or 100 mm petri dishes (Falcon, Lincoln Park, N.J.) at a concentration of 75 pmol/$cm^2$ as described by Patel and Lodish (1986), supra. Control plates were coated in analogous fashion with 2% (FN-free) bovine serum albumin (BSA, Boehringer Mannheim, Mannheim, Germany).

Retroviral infection protocol

Bone marrow samples from healthy adult donors were collected in tubes containing sterile, preservative-free sodium sulfate heparin according to protocols approved by the Institutional Review Board of Indiana University School of Medicine. Low density mononuclear cells were prepared by centrifugation on Ficoll-Hypaque (density 1.077 g/ml, Pharmacia, Piscataway, N.J.) for 45 minutes at 25° C. Plastic adherent cells were removed from low density bone marrow cells by an additional incubation on tissue culture plates for 4–16 hours at 37° C. in 5% $CO_2$ in IMDM with 2-% FCS.

Adherent-negative low density mononuclear cells were prestimulated prior to retroviral infection as described previously by Luskey et al. (1992) *Blood* 80:396, for 48 hours at 37° C. and 5% $CO_2$ in IMDM containing 20% FCS, 100 U/ml rhIL-6, 100 ng/ml rhSCF (both Amgen, Thousand Oaks, Calif.), and P/S at a cell density of $1\times10^6$ cells/ml in petri dishes. Prestimulated cells were harvested by vigorously pipetting to remove cells loosely adherent to the plastic.

Prestimulated cells ($5\times10^5$ cells/ml) were incubated for 6 hours on plates coated with BSA (control plates) or fibronectin or fragments thereof (subjected to UV radiation to better adhere the proteins to the plastic plate) and then infected with virus supernatant in the presence of growth factors (as above) and 7.5 micrograms/ml polybrene (Aldrich Chemical, Milwaukee, Wis.). Virus supernatant was replaced (including growth factors and 5.0 microgram/ml polybrene) after 2 hours and cells were incubated for an additional 12 to 24 hours. Non-adherent cells were re-added with each media change.

Following the infection protocol, non-adherent cells were decanted and adherent hematopoietic cells were collected from the cultures using Cell Dissociation Buffer (CDB) (enzyme free/PBS based, Gibco) according to the manufacturer's instructions. The adherent cells were added to the non-adherent fraction, washed twice and counted. Harvested cells were either plated in clonogenic methylcellulose progenitor assays or long term bone marrow cultures.

Long term bone marrow cultures

LTC-IC (human stem cell) assays were performed according to previously described methods with slight modifications. Sutherland et al. (1989) Blood 74:1563. Briefly, $0.5-1\times10^6$ infected cells were seeded in long term bone marrow cultures (LTMC) on confluent, pre-irradiated (as above) allogenic human bone marrow fibroblasts (BMF) in 5 ml IMDM containing 10% FCS, 10% horse serum (Sigma) and P/S, $1\times10^{-5}$ M hydrocortisone (Upjohn, Kalamazoo, Mich.), and 320 mosmol sodium chloride in 6 well tissue culture plates (Costar, Cambridge, Mass.). LTMC were incubated at 33° C. in 5% $CO_2$ and fed weekly by removal of 50% of the media and non-adherent cells. After five weeks, LTC-IC cultures were sacrificed by using CDB to remove adherent hematopoietic cells from BMF. Both non-adherent and adherent hematopoietic cells were combined and plated in methylcellulose to obtain colonies derived from LTC-IC.

Clonogenic methylcellulose assays

Methylcellulose assays were performed as previously described by Toksoz et al. (1992) Proc, Natl. Acad. Sci., USA 89:7350, with minor modifications. Briefly, $2-5\times10^4$ infected adult bone marrow cells were plated with 5 units/ml erthropoietin (Epo, Amgen), 100 ng/ml rhSCF, 10 ng/ml rhIL-3 (Genzyme, Cambridge, Mass.) in 1 ml of 2.4% IMDM methylcellulose (Fluka, Ronkonkoma, N.Y.) containing 25% FCS, 10% human plasma, $10^{-5}$ M beta- mercaptoethanol (Sigma), and P/S. Cultures were incubated at 37° C. in 5% $CO_2$/95% air and colonies (>50 cells) were scored by viewing on an inverted microscope on day 13 as CFU-GM (containing granulocytes and macrophages), CFU-Mix (containing myeloid and erythroid elements), or BFU-E (containing only erythroid elements).

Analysis of retroviral infection

Efficiency of infection with the TKNEO virus was analyzed by determining the percent of methylcellulose colonies resistant to 1.5 mg/ml (dry powder, Gibco) G418 on day 13. Mock infections were performed in each experiment by incubating bone marrow on the GP+EnvAM 12 packaging line making no recombinant virus. Culture of these mock infected cells with 1.5 mg/ml G418 consistently demonstrated <1% background colonies.

Gene transfer efficiency into committed progenitor cells

Figure 2:
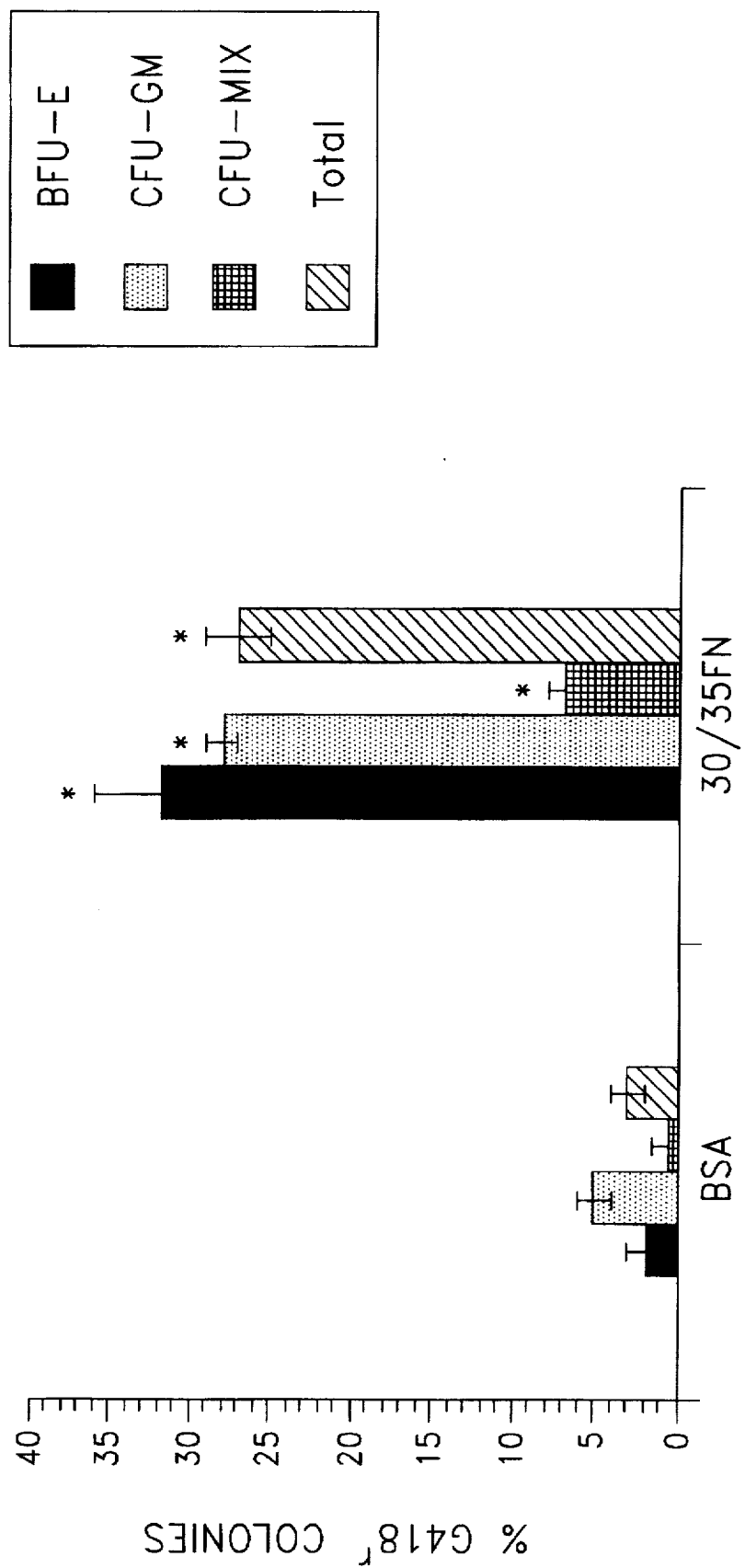
FIG. 2 shows the infection efficiency of committed human progenitor cells in the presence of 30/35 FN using the TKNEO vector.

Transduction efficiency was compared by infecting bone marrow cells while plated on 30/35 FN- or BSA-coated dishes. No difference in the number of colonies obtained after infection without selection was observed between these conditions. FIG. 2 demonstrates the percentage of G418$^r$ colonies after infection. A higher percentage of G418$^r$ colonies was noted on 30/35 FN from all types of progenitors, including those derived from lineage-restricted (BFU-E and CFU-GM) as well as multilineage (CFU-Mix) progenitor cells. Infection into all committed progenitors was increased 9-fold on 30/35 FN versus BSA.

Gene transfer efficiency into long term culture-initiating cells

Gene transfer into LTC-IC was assessed using the TKNEO vector. Gene transfer into LTC-IC derived colonies was only detected after infection on 30/35 FN (16% G418$^r$ vs 0% G418$^r$ colonies, 30/35 FN vs BSA).

Specificity of 30/35 FN effects on infection efficiency of hematopoietic cells

Figure 3:
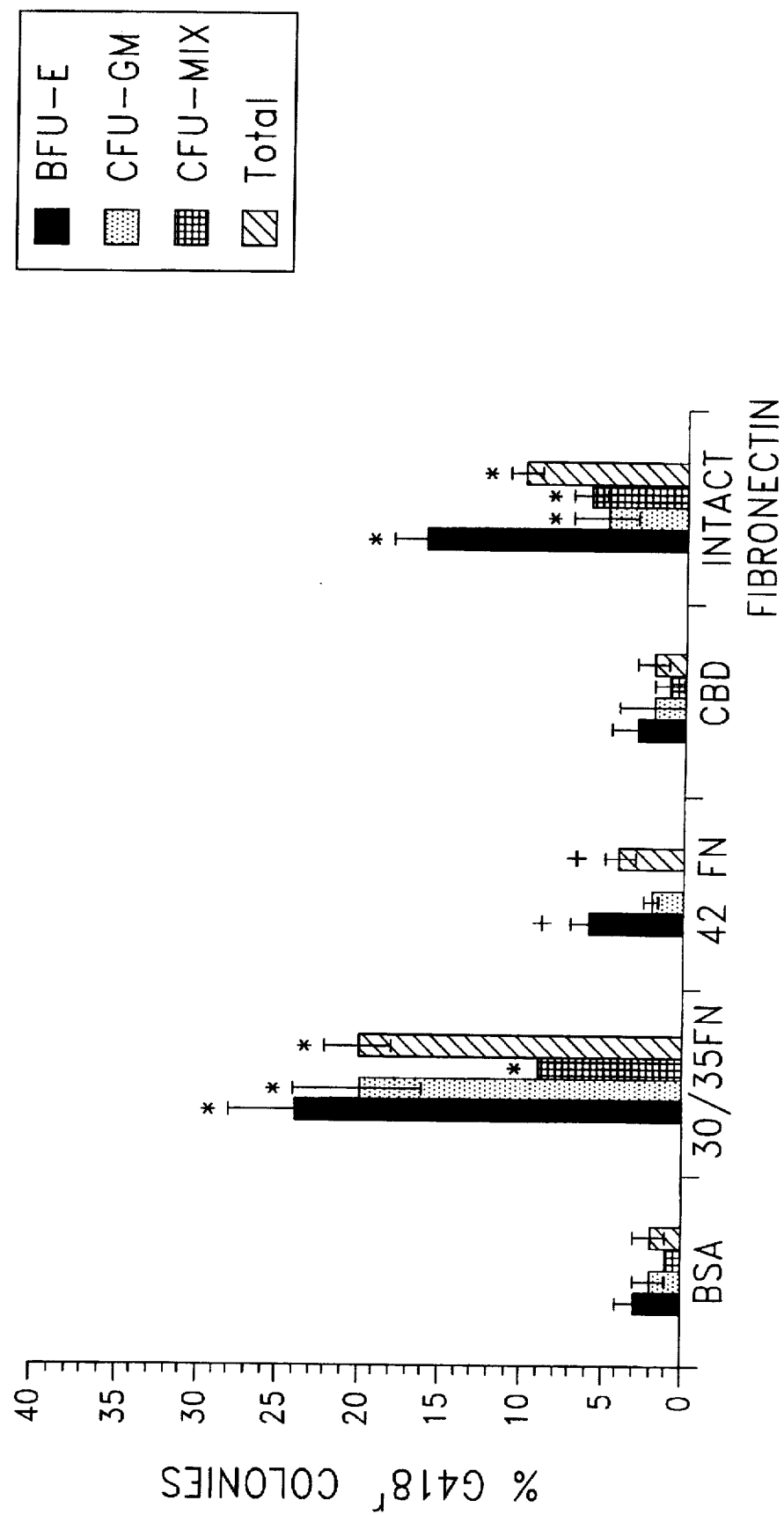
FIG. 3 compares the infection efficiency of committed progenitors in the presence of FN fragments using the TKNEO vector.

To determine the specificity of increased gene transfer efficiency seen on 30/35 FN, infection with TKNEO was performed on plates coated with BSA, 30/35 FN, intact fibronectin, a 115 kd FN fragment containing the central cell-binding domain (CBD) containing the RGDS tetrapeptide sequence, and a 42 kd C-terminal FN fragment (42 FN) characterized by the heparin II binding domain but lacking the CS-2 sequence (FIG. 1). Infection on BSA yielded 3±1% G418$^r$ BFU-E, 1±1% G418$^r$ CFU-GM, and 0±0% G418$^r$ CFU-MIX. No significant increase in the proportion of G418$^r$ colonies were noted on CBD, while slightly higher infection of BFU-E (6.0±-1%) were seen on 42 FN (FIG. 3). However, intact FN promoted increased gene transfer into all committed progenitors. The percentage of G418$^r$ colonies after infection on intact FN were less than on 30/35 FN in all lineages, including BFU-E (16±±2 vs. 24±4%), CFU-GM (5±2 vs 20±4%) and CFU-Mix (6±1 vs 9±1; intact FN vs 30/35 FN, respectively.

EXAMPLE 2

Gene Transfer into Bone Marrow Cells Using PGK-mADA

PGK-mADA virus supernatant was prepared as described for TKNEO in EXAMPLE 1. Chymotryptic fragments of fibronectin (FIG. 1) were prepared as previously described in EXAMPLE 1 and the retroviral infection protocol of EXAMPLE 1 was followed. LTC-IC (human stem cells) assays and Methylcellulose assays were performed according to EXAMPLE 1.

Analysis of retroviral infection

Efficiency of infection with the PGK-mADA vector was determined by protein analysis using ADA isoenzyme electrophoresis. Analysis of individual progenitor colonies was performed as previously described by Moritz (1993) and Lim et al. (1989) Proc. Natl. Acad. Sci., USA 86:8892. To stringently analyze transfer efficiency, only colonies expressing mADA at the same or a higher level than endogenous human ADA were considered transduced. For analysis of pooled colonies, colonies picked out of methylcellulose culture were combined in 1.5 ml microtubes (Rainin, Woburn, Mass.), washed with warm medium and phosphate buffered saline (PBS), centrifuged and stored at −20° C. For ADA analysis, cells were lysed in 5 microliter of lysis buffer by repeated freezing-thawing cycles and isoenzyme electrophoresis was performed as previously described.

Gene transfer efficiency into committed progenitor cells

Transduction efficiency was compared by infecting bone marrow cells while plated on 30/35 FN- of BSA-coated dishes. No difference in the number of colonies obtained after infection without selection was observed between these conditions. As shown in Table 1, infection efficiency into all committed progenitors was substantially increased on 30/35 FN vs BSA. As expected with the high titer ($\sim 1\times 10^7$ virons/ml) vector, the transduction efficiency of committed progenitors was extremely high. Referring to Table I, infection of bone marrow on 30/35 FN with PGK-mADA yielded nearly 100% transduction of committed progenitors in two separate experiments.

TABLE 1

Infection efficiency of committed human progenitor cells on fibronectin 30/35 fragments using the PGK-mADA vector

|  | BSA | 30/35FN |
| --- | --- | --- |
| Exp 1 | 1/18* | 13/14 |
| Exp 2 | 2/13 | 12/13 |

*number of mADA expressing colonies/total colonies analyzed

Gene transfer efficiency into long term culture-initiating cells

In four independent experiments performed with PGK-mADA a significant proportion of progenitor colonies derived from 5 week old LTMC (i.e., LTC-IC derived colonies) expressed the transferred murine ADA gene. Expression ranged from 2/12 (17%) to 6/6 (100%) of analyzed colonies (Table 2). Expression of the introduced mADA gene exceeded or at least equaled the amount of endogenous human ADA activity in all colonies considered positive. Infection efficiency for PGK-mADA was higher than for TKNEO. As shown in Table 2, infection of bone marrow on 30/35 FN with PGK-mADA yielded nearly 100% transduction of committed progenitors in two separate experiments.

TABLE 2

Infection efficiency of human long term culture initiating cell (LTC-IC) using the PGK-mADA vector

|  | BSA | 30/35FN |
| --- | --- | --- |
| Exp 1 | 0/14* | 10/19 |
| Exp 2 | N/A | 2/12 |
| Exp 3 | 0/4 | 3/5 |
| Exp 4 | 0/4 | 6/6 |
| Total | 0/22 | 21/42 |

*number of mADA positive colonies/total colonies analyzed;
N/A: not analyzed

Specificity of 30/35 FN effects on infection efficiency of hematopoietic cells

Gene transfer efficiency into LTC-IC was increased on 30/35 FN. Due to the relatively small size of these secondary LTC-IC derived colonies, the ability to perform protein analysis on single colonies was limited. After infection with PGK-mADA on BSA, intact fibronectin and 42 FN 0/6, 0/4, and 0/3 LTC-IC-derived colonies, respectively, demonstrated expression of murine ADA, while 3/5 LTFC-IC-derived colonies infected on 30/35 FN expressed mADA. In addition, when multiple LTC-IC-derived colonies were pooled before analysis in two additional experiments, mADA expression was detected only after infection on 30/35 FN and to a lesser degree on intact FN, but not on 42FN or BSA.

EXAMPLE 3

Gene Transfer into Bone Marrow Cells Using PGK-hADA

PGK-hADA virus supernatant is prepared as described for TKNEO in EXAMPLE 1. Chymotryptic fragments of fibronectin (FIG. 1) are prepared as previously described in EXAMPLE 1 and the retroviral infection protocol of EXAMPLE 1 was followed. LTC-IC and methylcellulose assays were performed as described in EXAMPLE 1.

Analysis of retroviral infection

For analysis of pooled colonies, colonies picked out of methylcellulose culture are combined in 1.5 ml microtubes (Rainin, Woburn, Mass.), washed with warm medium and PBS, centrifuged and stored at −20° C. For ADA analysis, cells are lysed in 5 microliter of lysis buffer by repeated freezing-thawing cycles and isoenzyme electrophoresis is performed as previously described.

EXAMPLE 4

Gene Transfer into Cord Blood Cells Using TKNEO

TKNEO virus supernatant and chymotryptic fragments of fibronectin (FIG. 1) were prepared as previously described in EXAMPLE 1. The retroviral infection protocol in EXAMPLE 1 was followed except that umbilical cord blood from normal, full term newborn infants was collected in tubes containing heparin according to protocols approved by the Institutional Review Board of Indiana University School of Medicine. LTC-IC (human stem cell) and methylcellulose assays were performed according to EXAMPLE 1.

Gene transfer efficiency into committed progenitors

Infection on FN30/35 was more than four times increased compared to BSA in three separate experiments (Table 3).

TABLE 3

INFECTION EFFICIENCY OF CORD BLOOD PROGENITOR CELLS USING 30/35 FN FRAGMENT AND TKNEO VECTOR

| BSA | 12 ± 17 |
| --- | --- |
| 30/35 | 55 ± 16 |

Gene Transfer into Cord Blood Cells Using PGK-mADA

PGK-mADA virus supernatant and chymotryptic fragments of fibronectin (FIG. 1) were prepared as previously described in EXAMPLE 1. The retroviral infection protocol in EXAMPLE 1 was followed except that cord blood from normal, full term newborn infants was collected in tubes containing heparin according to protocols approved by the Institutional Review Board of Indiana University School of Medicine. LTC-IC and methylcellulose assays were performed according to EXAMPLE 1.

Gene transfer efficiency into long-term culture initiating cells

Using the higher titer PGK-mADA vector, analysis of LTC-IC-derived colonies demonstrated high level expression of the introduced mADA cDNA only from cultures established from cord blood infected using supernatant on FN30/35. Little expression of mADA was detected in LTC-IC-derived colonies infected in BS control plates.

The results shown in EXAMPLES 4 and 5 demonstrate that improved infection efficiency using FN30/35 can also be achieved when using cord blood progenitor and stem cells.

EXAMPLE 6

Gene Transfer into Cord Blood Cells Using PGK-hADA

PGK-hADA virus supernatant and chymotryptic fragments of fibronectin (FIG. 1) is prepared as described for TKNEO in EXAMPLE 1. The retroviral infection protocol in EXAMPLE 1 is followed except that cord blood from normal, full term newborn infants is collected in tubes containing heparin according to protocols approved by the Institutional Review Board of Indiana University School of Medicine. LTC-IC and methylcellulose assays are performed according to EXAMPLE 1.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

All publications cited herein are hereby incorporated by reference in their entirety as if each had been individually incorporated by reference and fully set forth.

What is claimed is:

1. A method for increasing the frequency of transduction of hematopoietic cells by a replication-defective recombinant retrovirus vector, comprising infecting hematopoietic cells with a replication-defective recombinant retrovirus vector in the presence of substantially pure fibronectin, substantially pure fibronectin fragments, or a mixture thereof, so as to increase the frequency of transduction of the hematopoietic cells by the retrovirus vector.

2. The method of claim 1 wherein the hematopoietic cells have a protein deficiency or abnormality and the recombinant retrovirus vector includes an exogenous gene encoding the protein.

3. The method of claim 1 wherein the cells are infected with the retrovirus vector in the presence of a fibronectin fragment containing the alternatively spliced CS-1 cell adhesion domain.

4. The method of claim 1 wherein the hematopoietic cells are a human hematopoietic cellular population including human stem cells.

5. The method of claim 2 wherein the exogenous gene is a gene encoding adenosine deaminase.

6. The method of claim 5 wherein the exogenous gene is a gene encoding human adenosine deaminase.

7. The method of claim 4 wherein the hematopoietic cells are adherent-negative, low density, mononuclear cells.

8. A method for producing transduced hematopoietic cells, comprising:

infecting hematopoietic cells in culture with a replication-defective recombinant retrovirus in the presence of immobilized fibronectin, immobilized fibronectin fragments, or an immobilized mixture thereof, to produce transduced hematopoietic cells.

9. The method of claim 8 which includes harvesting the transduced hematopoietic cells.

10. The method of claim 8 wherein the hematopoietic cells have a protein deficiency or abnormality and the recombinant retrovirus vector includes an exogenous gene encoding the protein.

11. The method of claim 8 wherein the hematopoietic cells have an enzyme deficiency or abnormality and the exogenous gene is a gene encoding the enzyme.

12. The method of claim 11 wherein the hematopoietic cells are human hematopoietic cells having an enzyme deficiency or abnormality and the exogenous gene is a human gene encoding the enzyme.

13. The method of claim 11 wherein the hematopoietic cells have an adenosine deaminase deficiency and the exogenous gene encodes adenosine deaminase.

14. The method of claim 12 wherein the human hematopoietic cells have an adenosine deaminase deficiency and the exogenous gene encodes adenosine deaminase.

15. The method of claim 12 wherein the cells are infected with the retrovirus in the presence of an immobilized fibronectin fragment containing the alternatively spliced CS-1 cell adhesion domain.

16. The method of claim 15 wherein the hematopoietic cells are a human hematopoietic cellular population including human stem cells.

17. The method of claim 16 wherein the hematopoietic cells are adherent-negative, low density, mononuclear cells.

18. A method for improving retroviral-mediated gene transfer in hematopoietic cells, comprising conducting the retroviral-mediated gene transfer in the presence of immobilized fibronectin, immobilized fibronectin fragments or an immobilized mixture thereof.

19. The method of claim 18 wherein the hematopoietic cells are a mammalian hematopoietic cellular population including mammalian stem cells.

20. A composition comprising:

a viable hematopoietic cellular population transduced by retroviral-mediated gene transfer; and immobilized fibronectin, immobilized fibronectin fragments, or an immobilized mixture thereof, in the presence of which said population has been transduced by the retroviral-mediated gene transfer;

said composition being free from virus-producing cells.

21. The composition claim 20 wherein the cellular population is a human hematopoietic cellular population including human stem cells.

22. The composition of claim 20 wherein the hematopoietic cellular population is comprised of adherent-negative, low-density mononuclear cells.

* * * * *

UNITED STATES PATENT AND TRADEMARK OFFICE
CERTIFICATE OF CORRECTION

PATENT NO. : 5,686,278
DATED : November 11, 1997
INVENTOR(S) : David Williams et al.

It is certified that error appears in the above-indentified patent and that said Letters Patent is hereby corrected as shown below:

In col. 6, line 34, please delete the "s" after the word "fragment".

In col. 8, line 28, please delete "16++2" and insert in lieu thereof --16 $\pm$ -2--.

In col. 10, immediately below Table 3 and before the words "Gene Transfer into Cord Blood Cells Using PGK-mADA", please insert --EXAMPLE 5--.

In col. 12, line 39, claim 21, please add --of-- in between the words "composition" and "claim".

Signed and Sealed this

Tenth Day of March, 1998

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,686,278
DATED : November 11, 1997
INVENTOR(S) : David Williams et al.

It is certified that error appears in the above-identified patent and that said Letters Patent is hereby corrected as shown below:

On the title page, item [73] Assignee please add --Northwestern Western University, Evanston, Ill.-- as the Co-Assignee.

Signed and Sealed this

Twelfth Day of January, 1999

*Attest:*

*Attesting Officer*   Acting Commissioner of Patents and Trademarks